(12) United States Patent
DeLuca et al.

(10) Patent No.: US 7,419,992 B2
(45) Date of Patent: Sep. 2, 2008

(54) USE OF ARYL HYDROCARBON RECEPTOR LIGAND AS A THERAPEUTIC INTERVENTION IN ANGIOGENESIS-IMPLICATED DISORDERS

(75) Inventors: Hector F. DeLuca, Deerfield, WI (US); Margaret Clagett-Dame, Deerfield, WI (US); Jiasheng Song, Madison, WI (US); Stuart Helfand, Corvallis, OR (US); Nasim Akhtar, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 149 days.

(21) Appl. No.: 11/402,581

(22) Filed: Apr. 10, 2006

(65) Prior Publication Data

US 2007/0043092 A1 Feb. 22, 2007

Related U.S. Application Data

(63) Continuation-in-part of application No. 11/286,537, filed on Nov. 23, 2005, now Pat. No. 7,241,900, which is a continuation of application No. 10/364,253, filed on Feb. 11, 2003, now Pat. No. 7,002,019, and a continuation-in-part of application No. 10/074,102, filed on Feb. 12, 2002, now Pat. No. 6,916,834.

(60) Provisional application No. 60/356,585, filed on Feb. 12, 2002, provisional application No. 60/268,809, filed on Feb. 14, 2001.

(51) Int. Cl.
*A61K 31/427* (2006.01)
*A61K 31/405* (2006.01)

(52) U.S. Cl. .................. 514/365; 514/414; 514/419

(58) Field of Classification Search .............. 514/365, 514/414, 419
See application file for complete search history.

(56) References Cited

U.S. PATENT DOCUMENTS 3,285,931 A  11/1966  Husigen
6,323,228 B1  11/2001  BaMaung

FOREIGN PATENT DOCUMENTS

JP        11269175    * 10/1999
WO       WO 94/02483    2/1994

OTHER PUBLICATIONS

Pandya et al. Vascular Pharmacology, vol. 44, (2006), p. 265-274.*
Adachi J, et al. "Indirubin and indigo are potent aryl hydrocarbon receptor ligand present in human urine," J. Biol. Chem. 276:31475-31478 (2001).
Chen I, et al., "Indole-3-carbinol and diindolylmethane as aryl hydrocarbon (Ah) receptor agonists and antagonists in T47D human breast cancer cells," Biochem. Pharmacol. 51:1069-1076 (1996).
Chen Y, et al., "Regulation of CYP1A1 by indolo[3,2-b]carbazole in murine hepatoma cells," J. Biol. Chem. 270:22548-22555 (1995).
Cheung Y, et al., "Interaction with the aromatic hydrocarbon receptor, cyp1a induction, and mutagenicity of a series of diaminotoluenes—implications for their carcinogenicity," Toxicol. Appl. Pharmacol. 139:203-211 (1996).
Garrison P, et al., "Species-specific recombinant cell lines as bioassay systems for the detection of 2,3,7,8-tetrachlorodibenzo-p-dioxin-like chemicals," Fund. Appl. Toxicol. 30:194-203 (1996).
Heathpagliuso S, et al. "Activation of the Ah receptor by tryptophan and tryptophan metabolites," Biochem. 37:11508-11515 (1998).
Jellinck P, et al., "Ah receptor binding properties of indole carbinols and induction of hepatic estradiol hydroxylation,". Biochem. Pharmacol. 45:1129-1136 (1993).
Kleman M, et al., "Regulation of human dioxin receptor function by indolocarbazoles, receptor ligands of dietary origin,". J. Biol. Chem. 269:5137-5144 (1994).
Lee I, et al., "Transcriptional induction of the cytochrome p4501a1 gene by a thiazolium compound, yh439," Mol. Pharmacol. 49:980-988 (1996).
Liu R, et al., "Regulation of [Ah] gene battery enzymes and glutathione levels by 5,10-dihydroindeno[1,2-b]indole in mouse hepatoma cell lines," Carcinogenesis. 15:2347-2352 (1994).
Phelan D, et al. "Activation of the Ah receptor signal transduction pathway by bilirubin and biliverdin," Arc. Biochem. Biophy. 357:155-163 (1998).
Poellinger L, "Mechanistic aspects-the dioxin (aryl hydrocarbon) receptor," Food Add. Contam. 17:261-266 (2000).
Poland A & Glover E, "Chlorinated dibenzo-p-dioxin: Potent inducers of delta-aminolevulinic acid synthetase and aryl hydrocarbon hydroxylase. II. A study of the structure-activity relationship," Mol. Pharmacol. 9:736-747 (1973).
Rannung A, et al., "Certain photooxidized derivatives of tryptophan bind with very high affinity to the Ah receptor and are likely to be endogenous signal substances," J. Biol. Chem. 262:15422-15427 (1987).
Schaldach C, et al., "Lipoxin A(4): A new class of ligand for the Ah receptor," Biochem. 38:7594-7600 (1999).
Sinal C & Bend, J, "Aryl hydrocarbon receptor-dependent induction of cyp1a1 by bilirubin in mouse hepatoma hepa 1c1c7 cells," Mol. Pharmacol. 52(4):590-599 (1997).
Stephensen P, et al., "N-methoxyindole-3-carbinol is a more efficient inducer of cytochrome P-450 1A1 in cultured cells than indol-3-carbinol," Nutr Cancer Internatl. J. 36(1):112-121 (2000).
Vasiliou V, "Response of [Ah] battery genes to compounds that protect against menadione toxicity," Biochem. Pharmacol. 50(11):1885-1891 (1995).
Washburn B, et al. "Brevetoxin-6 (pbtx-6), a nonaromatic marine neurotoxin, is a ligand of the aryl hydrocarbon receptor," Arc. Biochem. Biophy. 343(2):149-156 (1997).
Whitlock J, "Genetic and molecular aspects of 2,3,7,8-tetrachlorodibenzo-p-dioxin action," Ann. Rev. Pharmacol. Toxicol. 30:251-277 (1990).
North M & Pattenden G, "Synthetic studies towards cyclic peptides. Concise synthesis of thiazoline and thiazole containing amino acids," Tetrahedron 46:8267-8290 (1990).

* cited by examiner

*Primary Examiner*—Rebecca L Anderson
*Assistant Examiner*—Yong Chu
(74) *Attorney, Agent, or Firm*—Quarles & Brady LLP

(57) ABSTRACT

A method of treating angiogenesis-implicated disorders by selecting a subject predisposed to an angiogenesis-implicated disorder and then administering an effective amount of an endogenous aryl hydrocarbon receptor ligand or its analogs according to a formula as disclosed herein is disclosed.

12 Claims, 2 Drawing Sheets

Vehicle  ITE

USE OF ARYL HYDROCARBON RECEPTOR LIGAND AS A THERAPEUTIC INTERVENTION IN ANGIOGENESIS-IMPLICATED DISORDERS

CROSS-REFERENCE TO RELATED APPLICATIONS

This application is a continuation-in-part of U.S. application Ser. No. 11/286,537, filed Nov. 23, 2005 now U.S. Pat. No. 7,241,900, which is a continuation of U.S. application Ser. No. 10/364,253, filed Feb. 11, 2003, now U.S. Pat. No. 7,002,019, which claims the benefit of U.S. Provisional Application No. 60/356,585, filed Feb. 12, 2002, and also is a continuation-in-part of U.S. application Ser. No. 10/074,102, filed Feb. 12, 2002, now U.S. Pat. No. 6,916,834, which claims the benefit of U.S. Provisional Application No. 60/268,809, filed Feb. 14, 2001.

STATEMENT REGARDING FEDERALLY SPONSORED RESEARCH OR DEVELOPMENT

BACKGROUND

The invention relates generally to a method of treating angiogenesis-implicated disorders, and more particularly to a method of treating angiogenesis-implicated disorders with an endogenous aryl hydrocarbon receptor ligand or one of its analogs.

Aryl Hydrocarbon Receptor. The aryl hydrocarbon receptor (AhR) is a ligand-inducible transcription factor that mediates a broad spectrum of physiological processes upon binding to its ligand. AhR was proposed and evidenced in the 1970's (Poland et al., 1976); whereas, the coding sequence for the receptor was cloned in the 1990's, revealing that the receptor is a member of an emerging basic Helix-Loop-Helix/Per-Arnt-Sim (bHLH/PAS) transcription factor super family (Burbach et al., 1992).

Upon binding to its ligand, a liganded AhR translocates from a cell's cytoplasm to its nucleus. Inside the nucleus, the liganded AhR forms a heterodimer with Ah receptor nuclear translocator (Arnt). The heterodimer then binds to a regulatory element, Ah response element (AhRE), within target genes either to enhance or to attenuate transcription of these genes. Responses mediated by AhR include expression of P450 family genes, cell proliferation or differentiation, apoptosis, immune suppression, vitamin A depletion, inhibition of adipose differentiation, waste syndrome, vascular development and remodeling, tumorigenicity or anti-tumorigenicity, and estrogenicity or anti-estrogenicity (Schmidt & Bradfield, 1996; Alexander et al., 1998; Whitlock, 1999; Poellinger, 2000; Elizondo et al. 2000; Safe, 2001; Vorderstrasse et al., 2001; Nilsson & Hakansson, 2002; Safe & Wormke, 2003; Walisser et al., 2004; Puga et al., 2005). Additionally, AhR-deficient mice show potential physiological function of AhR in liver, heart, ovary and immune system development (Femandez-Salguero et al., 1995; Schmidt et al., 1996; Mimura et al., 1997; Benedict et al., 2000).

A Recently Identified Physiological Ligand for AhR. To date, the AhR system has been studied with artificial ligands such as polycyclic aromatic hydrocarbons including 3-methylcolanthrene (3-MC), benzo[α]pyrene (BP) and halogenated aromatic hydrocarbons such as 2,3,7,8-tetrachlorodibenzo-p-dioxin (TCDD). While studies with these artificial ligands advance our understanding of the Ah receptor system, complete revelation of physiological roles the AhR plays and potential therapeutic benefits this system may provide necessitate the identification of its physiological ligand.

2-(1'H-indole-3'-carbonyl)-thiazole-4-carboxylic acid methyl ester (ITE) is a physiological ligand for the AhR that has been purified from procine lung and structurally identified (Song et al., 2002; U.S. Pat. No. 6,916,834). Not only has ITE been isolated from animals, but also it has been confirmed by chemical synthesis (Grzywacz et al., 2003).

Hypoxia-Inducible Factors and Arnt-Mediated Gene Expression. Hypoxia-inducible factor-1α (HIF-1α) and hypoxia-inducible factor-2α (HIF-2α) are also members of the bHLH/PAS transcription factor super family. Like AhR, HIF-1α and HIF-2α require Arnt to form a heterodimer to regulate transcription of their target genes. Under hypoxic conditions, both HIF-1α and HIF-2α are stabilized and their capability for transactivation are increased. Once activated, HIF-1α heterodimers and HIF-2α heterodimers affect transcription of over sixty genes involved in increasing oxygen delivery and activating alternative metabolic pathways (Tian et al., 1997; Giatromanolaki & Harris, 2001; Bracken et al., 2003; Quintero et al., 2004). One mechanism of increasing oxygen delivery through HIF-1α- and HIF-2α-mediated transcription is angiogenesis.

Angiogenesis. Angiogenesis is the generation of new blood vessels from existing ones and is a complex biological process involving a delicate balance of pro-angiogenic factors and anti-angiogenic factors. Pro-angiogenic factors include, but are not limited to, vascular endothelial growth factor (VEGF), basic fibroblast growth factor (bFGF), platelet-derived growth factor (PDGF), placental growth factor (PIGF), epidermal growth factor (EGF), angiopoietins, angiogenin and angiotropin. Whereas, anti-angiogenic factors include, but are not limited to, pigment epithelium-derived factor (PEGF), angiostatin, endostatin and thrombospondin.

Under physiological conditions, such as in wound healing, in female reproduction and in cancer growth and metastasis, the pro-angiogenic factors dominate and lead to angiogenesis. The initial steps of angiogenesis include vasodilation and enhanced permeability and destabilization of a blood vessel wall. Endothelial cells, also present in blood vessels, then proliferate, migrate and form tubes. The tubes are stabilized by pericytes and vascular smooth muscle cells (Distler et al., 2003; Carmeliet, 2004).

AhR and Angiogenesis. Since AhR, HIF-1α and HIF-2α share a common dimerization partner, Arnt, and are members of the same transcription factor super family, an extensive cross-talk between them is expected. In relation to angiogenesis, AhR may compete for Arnt binding with HIF-1α and HIF-2α to modulate angiogenesis (Gradin et al., 1996; Chan et al., 1999; Giatromanolaki & Harris, 2001). However, AhR interacts with other systems, such as transforming growth factor α and β (TGFα and TGFβ, respectively), epidermal growth factor receptor (EGFR), growth hormone receptor (GHR) and estrogen receptor (ER) (Hudson et al., 1986; Choi et al., 1991; Lin et al., 1991; Bryant et al., 1997; Enan et al., 1998; Zaher et al., 1998; Carlson & Perdew, 2002; Davis et al., 2003; Safe & Wormke, 2003; Nukaya et al., 2004). Therefore, AhR may modulate angiogenesis through other unknown pathways.

AhR and Vascular Development and Remodeling. Studies with TCDD, an artificial ligand of AhR, showed reduced growth of common cardinal veins (CCV) in zebrafish during a period of forty-four to sixty-two hours post fertilization (Bello et al., 2004). TCDD also blocked the regression of CCV between eighty and ninety-six hours post fertilization (Ld.). Likewise, in chick embryos, TCDD inhibited VEGF-directed vasculogenesis using coronary endothelial tube formation and outgrowth as endpoints (Ivnitski-Steele & Walker, 2003). Furthermore, AhR-deficient mice have a patent ductus venosus in their livers (Lahvis et al., 2000).

Even mice expressing low levels of AhR (hypomorphs) had phenotypes similar to AhR-deficient mice (Walisser et al., 2004).

Angiogenesis-Implicated Disorders. Under physiological conditions, regulated angiogenesis occurs in wound healing, female reproductive cycles and embryonic development. Conversely, in pathophysiological conditions, unregulated angiogenesis occurs in disorders such as purpura, angioma, pallor and bone loss. Additionally, unregulated angiogenesis occurs in disorders such as growth and metastasis of cancers, eye diseases including blinding retinopathies, and chronic diseases such as psoriasis and rheumatoid arthritis.

Angiogenesis is also involved in many other disorders. For one, anti-angiogenic factors reduced adipose tissue in obese mice (Li et al., 2002; Rupnick et al., 2002). Additionally, bacterial and viral pathogens induced angiogenic genes to advance pathological processes (Meyer et al., 1999; Harada et al., 2000). Furthermore, angiogenesis occurs in atherosclerosis, restenosis, transplant arteriopathy, warts, allergic dermatitis, keloids, peritoneal adhesions, synovitis, osteomyelitis, asthma, nasal polyps, choriodal and intraocular disorders, acquired immune deficiency, endometriosis, uterine bleeding and ovarian cysts (Carmeliet, 2004).

Therapeutic Inhibition of Angiogenesis. Endothelial cells (EC) are an attractive target for anti-angiogenesis therapy in angiogenesis-implicated disorders. For one, EC are involved in the early stages of angiogenesis. Additionally, EC are in direct contact with the blood and are therefore easily accessible. Furthermore, EC are genetically stable and are a homogenous diploid cell. As such, EC are less likely to develop acquired drug resistance to anti-angiogenic therapy (Folkman, 1995; Boehm et al., 1997).

Many anti-angiogenic agents are known. These agents are generally proteins, peptides or small molecules. Examples of these agents include, but are not limited to, anti-VEGF antibodies, anti-VEGFR antibodies, inhibitors of receptor tyrosine kinases such as VEGFR1, VEGFR2, PDGFR, bFGFR and EGFR, angiostatin, endostatin, fumagilin or its derivatives, and integrin inhibitors (Eskens, 2004). Despite the existence of these anti-angiogenic agents, there is a continued demand for new anti-angiogenic agents that are safe and effective.

SUMMARY

We disclose herein a method for therapeutic application of an AhR ligand for treatment of angiogenesis-implicated disorders.

In a first aspect the invention is a method for treating angiogenesis-implicated disorders. The method comprises the first step of selecting a subject predisposed to an angiogenesis-implicated disorder. The method comprises the second step of administering an effective amount of an AhR ligand having a formula of:

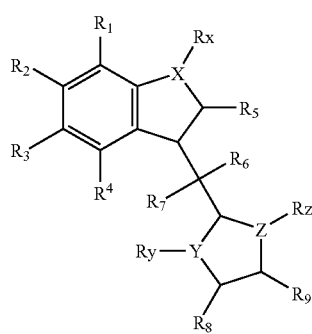

wherein:
$R_1$, $R_2$, $R_3$ and $R_4$ can be independently selected from the group consisting of hydrogen, halo, hydroxy (—OH), thiol (—SH), cyano (—CN), formyl (—CHO), alkyl, haloalkyl, alkenyl, alkynyl, amino, nitro (—NO$_2$), alkoxy, haloalkoxy, thioalkoxy, alkanoyl, haloalkanoyl and carbonyloxy.

$R_5$ can be selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

$R_6$ and $R_7$ together can be =O. Alternatively, $R_6$ can be selected from the group consisting of hydrogen, halo, cyano, formyl, alkyl, haloalkyl, alkenyl, alkynyl, alkanoyl and haloalkanoyl, and $R_7$ is independently selected from the group consisting of hydrogen, halo, hydroxy, thiol, cyano, formyl, alkyl, haloalkyl, alkenyl, alkynyl, amino, nitro, alkoxy, haloalkoxy, thioalkoxy, alkanoyl, haloalkanoyl and carbonyloxy. Alternatively, $R_7$ can be selected from the group consisting of hydrogen, halo, cyano, formyl, alkyl, haloalkyl, alkenyl, alkynyl, alkanoyl and haloalkanoyl, and $R_6$ is independently selected from the group consisting of hydrogen, halo, hydroxy, thiol, cyano, formyl, alkyl, haloalkyl, alkenyl, alkynyl, amino, nitro, alkoxy, haloalkoxy, thioalkoxy, alkanoyl, haloalkanoyl and carbonyloxy.

$R_8$ and $R_9$, independently, can be

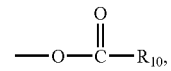

and $R_{10}$ is selected from the group consisting of hydrogen, halo, cyano, alkyl, haloalkyl, alkenyl and alkynyl.

Alternatively, $R_8$ and $R_9$, independently, can be

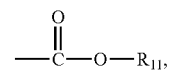

and $R_{11}$ is selected from the group consisting of hydrogen, halo, alkyl, haloalkyl, alkenyl and alkynyl.

Alternatively, $R_8$ and $R_9$, independently, can be

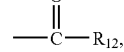

and $R_{12}$ is selected from the group consisting of hydrogen, halo, hydroxy, thiol, cyano, alkyl, haloalkyl, alkenyl, alkynyl, amino and nitro.

Alternatively, $R_8$ and $R_9$, independently, can be

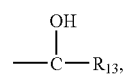

and $R_{13}$ is selected from the group consisting of hydrogen, halo, alkyl, haloalkyl, alkenyl and alkynyl.

Alternatively, $R_8$ and $R_9$, independently, can be selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

X can be oxygen or sulfur, and Rx is nothing. Alternatively, X can be nitrogen, and $R_x$ is selected from the group consisting of hydrogen, halo, formyl, alkyl, haloalkyl, alkenyl, alkynyl, alkanoyl, haloalkanoyl and a nitrogen protective group. Alternatively, X can be carbon, and $R_x$ is selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

Y can be oxygen or sulfur, and $R_y$ is nothing. Alternatively, Y can be nitrogen, and $R_y$ is selected from the group consisting of hydrogen, halo, formyl, alkyl, haloalkyl, alkenyl, alkynyl, alkanoyl, haloalkanoyl and a nitrogen protective group. Alternatively, Y can be carbon, and $R_y$ is selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

Z can be oxygen or sulfur, and $R_z$ is nothing. Alternatively, Z is nitrogen, and $R_z$ is selected from the group consisting of hydrogen, halo, formyl, alkyl, haloalkyl, alkenyl, alkynyl, alkanoyl, haloalkanoyl and a nitrogen protective group. Alternatively, Z can be carbon, and $R_z$ is selected from hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

In a preferred embodiment of the first aspect, the aryl hydrocarbon receptor ligand has a formula of:

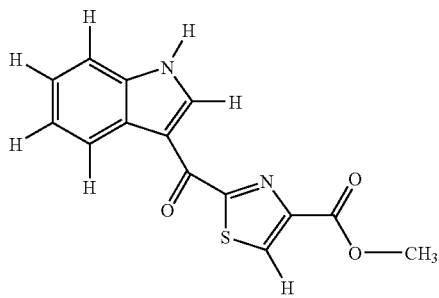

In another preferred embodiment of the first aspect, the aryl hydrocarbon receptor ligand has a formula of:

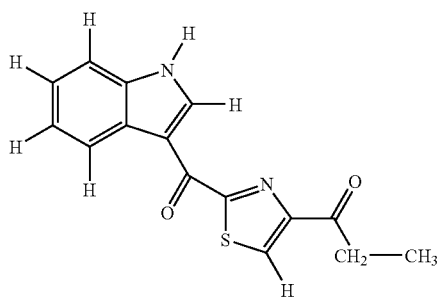

In an additional preferred embodiment of the first aspect, the angiogenesis-implicated disorder is either a retinopathy, psoriasis, rheumatoid arthritis, obesity or cancer.

In a further preferred embodiment of the first aspect, the step of administering the aryl hydrocarbon receptor ligand is selected from the group consisting of capsules, creams, lozenges, tablets and injection.

The previously described embodiments of the present invention have many advantages, including a first advantage that a patient is less prone to induce acquired drug resistance.

A second advantage of the present invention is that it eliminates the side-effects of dioxins.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

The invention will be better understood and features, aspects and advantages other than those set forth above will become apparent when consideration is given to the following detailed description thereof. Such detailed description makes reference to the following drawings, wherein:

FIG. 1 shows angiogenesis in mouse corneas in response to bFGF stimulation and intra-peritoneal (i.p.) injection of either vehicle (DMSO:propylene glycol, 1:1, v/v) or 10 µg/µl of ITE in vehicle, wherein FIG. 1A1 through FIG. 1A3 show corneas from three mice injected with vehicle, wherein FIG. 1A4 through FIG. 1A6 show corneas from three mice injected with 10 µg/µl of ITE in vehicle, and wherein FIG. 2 shows dose-response effects of different concentrations of ITE on angiogenesis in mouse corneas in response to bFGF stimulation with i.p. injection of either vehicle or different concentrations of ITE in vehicle, wherein FIG. 2A1 through 2A4 show corneas from four mice injected with vehicle, wherein FIG. 2A5 through FIG. 2A7 show corneas from three mice injected with 2 µg/µl of ITE in vehicle, wherein FIG. 2A8 through 2A12 show corneas from five mice injected with 5 µg/µl of ITE in vehicle, wherein FIG. 2A13 through FIG. 2A17 show corneas from five mice injected with 10 µg/µl of ITE in vehicle, and wherein

DESCRIPTION OF PREFERRED EMBODIMENTS

Figure 1A:
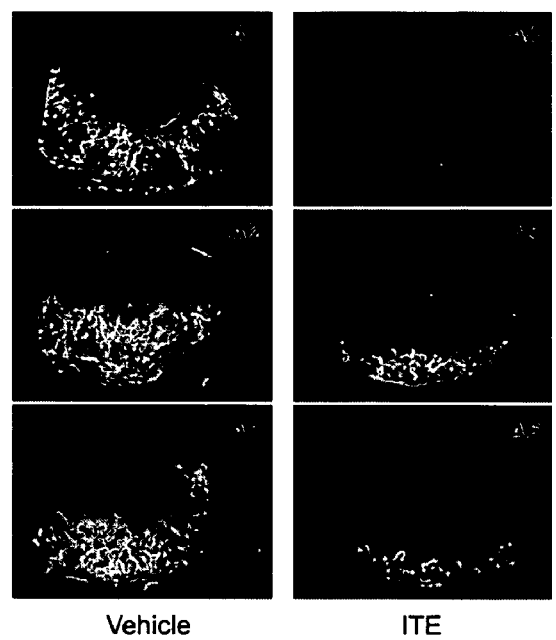

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, the preferred methods and materials are described below.

As used herein, "angiogenesis-implicated disorder" refers to any disorder associated with the concurrent process of angiogenesis or depending on angiogenesis for its occurrence and progression.

As used herein, "an effective amount" is defined as that concentration of ligand, such as ITE, to attenuate angiogenesis by at least 50% as measured by the procedure described in Examples.

As used herein, "analog" is defined as a compound with structural similarity to ITE that is within the general formula.

As used herein, "alkyl" refers to a group of hydrogen saturated one to six carbons connected in either straight or branched fashion.

As used herein, "haloalkyl" refers to an alkyl substituted by one or more halogen atoms.

As used herein, "alkenyl" refers to a group of hydrocarbons containing two to six carbons connected in either straight or branched fashion with at least one carbon-to-carbon double bond.

As used herein, "alkynyl" refers to a group of hydrocarbons containing two to six carbons connected in either straight or branched fashion with at least one carbon-to-carbon triple bond.

As used herein, "amino" refers to —NRaRb where Ra and Rb can be independently selected from the group consisting of hydrogen, halo, formyl (—CHO), alkyl, haloalkyl, alkenyl, alkynyl, alkanoyl, haloalkanoyl and a nitrogen protective group.

As used herein, "halo" refers to any halogen atom (F, Cl, Br, or I).

As used herein, "alkanoyl" refers to an alkyl connected to the parent moiety through a carbonyl group, such as [—C(O)-alkyl].

As used herein, "haloalkanoyl" refers to a haloalkyl connected to the parent moiety through a carbonyl group, such as [—C(O)-haloalkyl].

As used herein, "carbonyl" refers to —C(O)—.

As used herein, "nitrogen protective group" refers to groups commonly used to protect nitrogen from undesired chemical reactions during synthesis procedures, such as —CH$_3$, —C(CHC$_3$)$_3$, —CH$_2$CN, and —CH$_2$C$_6$H$_4$OCH$_3$, etc.

As used herein, "alkoxy" refers to an alkyl connected to the parent structure through an oxygen atom, such as [—O-alkyl].

As used herein, "haloalkoxy" refers to a haloalkyl connected to the parent moiety through an oxygen atom, such as [—O-haloalkyl].

As used herein, "thioalkoxy" refers to an alkyl connected to the parent structure through a sulfur atom, such as [—S-alkyl].

As used herein, "carbonyloxy" refers to an alkanoyl connected to the parent moiety through an oxygen atom [—O—C(O)-alkyl].

The present invention is a method of therapeutic treatment of angiogenesis-implicated disorders including, but not limited to, retinopathies, psoriasis, rheumatoid arthritis, obesity, and growth and metastasis of cancers with AhR ligand and its analogs including, but not limited to, ITE and its analogs. The formula of ITE is as follows:

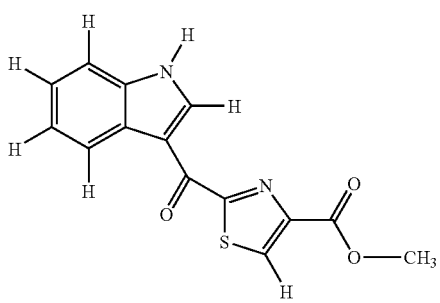

We envision that an especially useful analog of ITE will increase its stability and extend its half-life in animals, such as mammals, because a ketone has replaced the ester, an easy target for numerous esterases, on the original ITE structure. The extended half-life will certainly translate into higher potency in treatment of angiogenesis-implicated disorders. A specific preferable ITE analog is of the following formula:

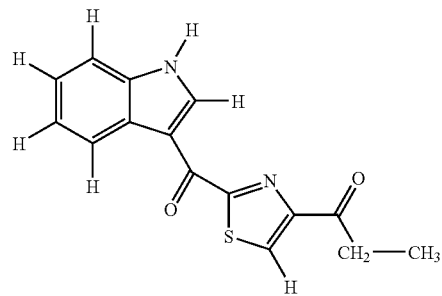

However, other analogs of ITE useful in therapeutic applications in treating angiogenesis-implicated disorders are ones corresponding to the following formula:

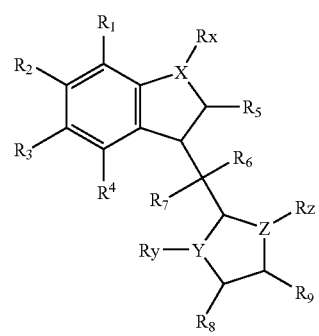

wherein:

$R_1$, $R_2$, $R_3$ and $R_4$ can be independently selected from the group consisting of hydrogen, halo, hydroxy (—OH), thiol (—SH), cyano (—CN), formyl (—CHO), alkyl, haloalkyl, alkenyl, alkynyl, amino, nitro (—NO2), alkoxy, haloalkoxy, thioalkoxy, alkanoyl, haloalkanoyl and carbonyloxy.

$R_5$ can be selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

$R_6$ and $R_7$ together can be =O. Alternatively, if $R_6$ is selected from the group consisting of hydrogen, halo, cyano, formyl, alkyl, haloalkyl, alkenyl, alkynyl, alkanoyl and haloalkanoyl, then $R_7$ is independently selected from the group consisting of hydrogen, halo, hydroxy, thiol, cyano, formyl, alkyl, haloalkyl, alkenyl, alkynyl, amino, nitro, alkoxy, haloalkoxy, thioalkoxy, alkanoyl, haloalkanoyl and carbonyloxy. Alternatively, if $R_7$ is selected from the group consisting of hydrogen, halo, cyano, formyl, alkyl, haloalkyl, alkenyl, alkynyl, alkanoyl and haloalkanoyl, then $R_6$ is independently selected from the group consisting of hydrogen, halo, hydroxy, thiol, cyano, formyl, alkyl, haloalkyl, alkenyl, alkynyl, amino, nitro, alkoxy, haloalkoxy, thioalkoxy, alkanoyl, haloalkanoyl and carbonyloxy.

$R_8$ and $R_9$, independently, can be

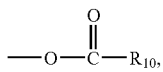

and $R_{10}$ is selected from the group consisting of hydrogen, halo, cyano, alkyl, haloalkyl, alkenyl and alkynyl.

Alternatively, $R_8$ and $R_9$, independently, can be

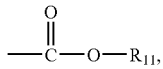

and $R_{11}$ is selected from the group consisting of hydrogen, halo, alkyl, haloalkyl, alkenyl and alkynyl.

Alternatively, $R_8$ and $R_9$, independently, can be

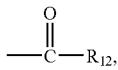

and $R_{12}$ is selected from the group consisting of hydrogen, halo, hydroxy, thiol, cyano, alkyl, haloalkyl, alkenyl, alkynyl, amino and nitro.

Alternatively, $R_8$ and $R_9$, independently, can be

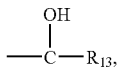

and $R_{13}$ is selected from the group consisting of hydrogen, halo, alkyl, haloalkyl, alkenyl and alkynyl.

Alternatively, $R_8$ and $R_9$, independently, can be selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

X can be oxygen or sulfur, and $R_x$ is nothing. Alternatively X can be nitrogen, and $R_x$ is selected from the group consisting of hydrogen, halo, formyl, alkyl, haloalkyl, alkenyl, alkynyl, alkanoyl, haloalkanoyl and a nitrogen protective group. Alternatively, X can be carbon, and $R_x$ is selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

Y can be oxygen or sulfur, and $R_y$ is nothing. Alternatively, Y can be nitrogen, and $R_y$ is selected from the group consisting of hydrogen, halo, formyl, alkyl, haloalkyl, alkenyl, alkynyl, alkanoyl, haloalkanoyl and a nitrogen protective group. Alternatively, Y can be carbon, and $R_y$ is selected from the group consisting of hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

Z can be oxygen or sulfur, and $R_z$ is nothing. Alternatively, Z is nitrogen, and $R_z$ is selected from the group consisting of hydrogen, halo, formyl, alkyl, haloalkyl, alkenyl, alkynyl, alkanoyl, haloalkanoyl and a nitrogen protective group. Alternatively, Z can be carbon, and $R_z$ is selected from hydrogen, halo, hydroxy, thiol, cyano, formyl, =O, alkyl, haloalkyl, alkenyl, alkynyl, amino, nitro, alkoxy, haloalkoxy, thioalkoxy, alkanoyl, haloalkanoyl and carbonyloxy.

As angiogenesis inhibitors, endogenous AhR ligands, including ITE and its analogs, are useful in the treatment of primary and metastatic cancers. Cancers cannot grow beyond the size of one to two cubic millimeters or cannot migrate from a primary site to other locations without an adequate supply of oxygen and nutrients and removal of metabolic wastes. Intuitively, that seems to be true only for those "solid" tumors. Some studies, however, revealed that advancement of leukemia and other "liquid" tumors may also rely on angiogenic processes, at least before they spread into the general circulation (Perez-Atayde et al., 1997). Thus, the applicability of anti-angiogenic therapy extends virtually to all types of cancer.

By targeting genetically stable endothelial cells responsible for the initial process of neovascularization, anti-angiogenesis therapy is less prone to induce acquired drug resistance, which is a challenge in conventional chemotherapy targeting genetically heterogeneous cancer cells. It is also advantageous for the anti-angiogenic therapy to target endothelial cells, which are in constant contact with the blood and thus are readily accessible to anti-angiogenic agents in general circulation.

ITE and its analogs may also possess anti-tumorigenic capability. Studies revealed that some AhR ligands with phytochemical origin, including some with an indole moiety, are anti-estrogenic and anti-tumorigenic (McDougal et al., 2001; Bradshaw et al., 2002; Safe & McDougal, 2002). Additionally, liganded AhR arrested cell cycle, promoted apoptosis and antagonized estrogen actions (Heimler et al., 1998; Elizondo et al., 2000; Puga et al., 2000; Safe & Wormke, 2003). Furthermore, AhR agonists inhibited pancreatic cancer cell lines with high AhR expression (Koliopanos et al., 2002). We believe that ITE and its analogs will be effective therapeutic agents in treating cancers though multiple mechanisms.

Like cancer, adipose tissue expansion also depends on angiogenesis. As reported, pro-angiogenic factors are stimulated by the growth of adipose tissue and inhibition of angiogenesis in mouse models resulted in body weight loss and in adipose tissue reduction (Li et al., 2002; Rupnick et al., 2002). Through inhibition of angiogenesis, we envision that ITE and its analogs will be useful in controlling body weight.

As noted previously, in vitro systems confirmed the inhibitory effects of TCDD/AhR on adipose differentiation (Alexander et al., 1998; Shimba et al., 2001). Recently, AhR was shown to affect feeding behavior of animals through regulation of SIM1, which is believed to be involved in hypothalamus functioning (Yang et al., 2004). Thus, it is advantageous to use AhR ligands and their analogs, including ITE and its analogs, in body weight control since they will work through more than one mechanism.

Retinopathies, such as diabetic retinopathy and retinopathy of prematurity, are major causes of blindness. Estimates show that nearly three-fourths of diabetic patients within fifteen years of onset of disease develop diabetic retinopathy (Klein et al., 1984; Sjolie et al., 1997). Similarly, retinopathy of prematurity is an ischemic proliferative retinopathy that leads to irreversible childhood blindness.

Current therapies to treat retinopathies include invasive procedures such as laser photocoagulation and cryotherapy. Unfortunately, these therapies cause side-effects including decreased peripheral vision, impaired night vision and changed color perception. In some cases, the disease continues to advance despite surgical intervention (Caldwell et al., 2003; Stout & Stout, 2003). As an effective angiogenesis inhibitor, endogenous AhR ligands, including ITE and its analogs, will be useful in medical intervention of blinding retinopathies.

Psoriasis and rheumatoid arthritis represent chronic, inflammatory, hyperproliferative diseases affecting approximately 2% of U.S. and world populations (Elder et al., 2001; Louie et al., 2003). Both are autoimmune disorders whose pathological advancements are aided by angiogenesis. Immune suppressants, such as cyclosporin, and anti-angiogenic agents are effective in therapeutic intervention in disease models (Oliver et al., 1995; Lebwohl et al., 1998; Powell et al., 1999; Sone et al., 2001). We envision that endogenous AhR ligands, including ITE and its analogs, will be effective therapy for these diseases not only because ITE is anti-angiogenic in vivo, but also because it may well be an effective immune suppressant (Vorderstrasse et al., 2001; Kerkvliet, 2002).

From implantation of a fertilized egg to further development of an embryo in a reproductive period of an adult mammal, a finely coordinated process including angiogenesis is a prerequisite for successful reproduction. Inhibition of angiogenesis at this critical moment would be a huge challenge to this process. It has been hypothesized, not surprisingly, that inhibition of angiogenesis may even provide a novel alternative for birth control (Zhang & Bicknell, 2001). Therefore, as anti-angiogenesis agents, AhR ligands, including ITE and its analogs, may be useful in contraception for humans and animals.

Dosing regimes for ITE and its analogs can be routinely determined in accordance with pharmacological activity data from in vivo experimental models. A pharmaceutical composition will be composed of ITE or its analogs (the active ingredients), pharmaceutically acceptable carrier(s), other compatible ingredients such as preservatives, and even other compatible therapeutic agents. Pharmaceutically acceptable carriers are inert materials useful for administering the active ingredients, preferably sterile and nontoxic, and compatible with the active ingredients and can be solid, liquid, or gas in nature. The pharmaceutical compositions can be administered orally and parenterally. The preparation can be provided in capsules, creams, lozenges, tablets or intravenously. Initial screening will be conducted by the procedure described below. Further screening procedures will be devised accordingly once a disease target is identified.

In an ideal treatment plan, the formulated ITE or its analogs will be administered either orally (capsules or tablets, for example) or parentally (topical application or injection, for example) by a human patient with a disorder mentioned above. The effective dosing range will be determined by the blood concentrations of ITE or its analogs achievable by a specific dosing regimen. The said concentrations in blood should be equivalent to those achieved in mice when dosed i.p. at 2 to 10 mg/kg body weight. The frequency of dosing will be decided by the kinetics of ITE and its analogs in the system. Currently, twice a day is proposed as preferable with ITE. The dosing will be continued until the patient is free from the disorder. It may be preferable to provide a maintenance dosing.

EXAMPLES

Example 1

Inhibition of Angiogenesis With Aryl Hydrocarbon Receptor Ligand: Mouse Corneal Grafting Assay Methods: Polyvinyl sponges (Rippey, Eldorado Hills, Calif.) pre-irradiated with 2,000 Gy from a cesium source are cut into 0.4×0.4×0.2 mm pieces and 100 ng of a bFGF (Sigma-Aldrich, St. Louis, Mo.) dissolved in Dulbecco's phosphate buffered saline without calcium or magnesium (DPBS; Cambrex, Walkersville, Md.) are introduced into each sponge using a syringe. The loaded sponges are then air-dried.

A female adult BALB/c mouse (~20 g in body weight; Harlan, Indianapolis, Ind.) is anesthetized with Avertin composed of tribromoethanol (Aldrich, Milwaukee, Wis.), tertiary amyl alcohol (Aldrich), ethanol, and distilled water in a ratio of 1:1:9.8:88.2 (w/v/v/v). One of the sponges are introduced into a surgically created micro-pocket in an avascular area of one cornea. Mice are put under a 75 W incandescent light bulb to recover from the effect of anesthesia.

The vehicle for delivering ITE is a 1:1 (v/v) mixture of dimethyl sulphoxide (DMSO; Sigma-Aldrich) and propylene glycol (Gallipot, St. Paul, Minn.). Intra-peritoneal injection of 20 µl of the vehicle or ITE in the vehicle is started at the same day. The injections are done twice a day for six consecutive days. On day 6, 200 µl of fluorescein 5(6)-isothiocyanate (FITC) conjugated with high molecular weight dextran (2,000,000 MW; Sigma-Aldrich) are injected into the tail vein. Mice are euthanized three to five minutes after the injection. Sponge-containing eyes are enucleated and fixed for 5 minutes with 4% paraformaldehyde. The cornea with the adjacent limbus are dissected, rinsed in DPBS, and mounted with 10% glycerol onto a glass slide.

A stereomicroscope with an epifluorescence attachment (Stemi SV11, Zeiss, Thornwood, N.Y.) is used to visualize the overall appearance of a cornea and the presence of the perfused blood vessels (appearing green). Images are digitally recorded with a Hitachi HV-C20U-S4 camera and saved as JPEG files. The saved images are analyzed with Adobe Photoshop 6.0 (Adobe Systems Inc., San Jose, Calif.). Intensities of green light of each pixel in an image is integrated and an average is taken as total average intensity. The background intensity of green light is estimated by cropping the background area of several images, integrating the intensities, and taking the average. The net average green light intensity of each image is then obtained by subtracting the background from the total average green light intensity and reported.

Figure 1B:
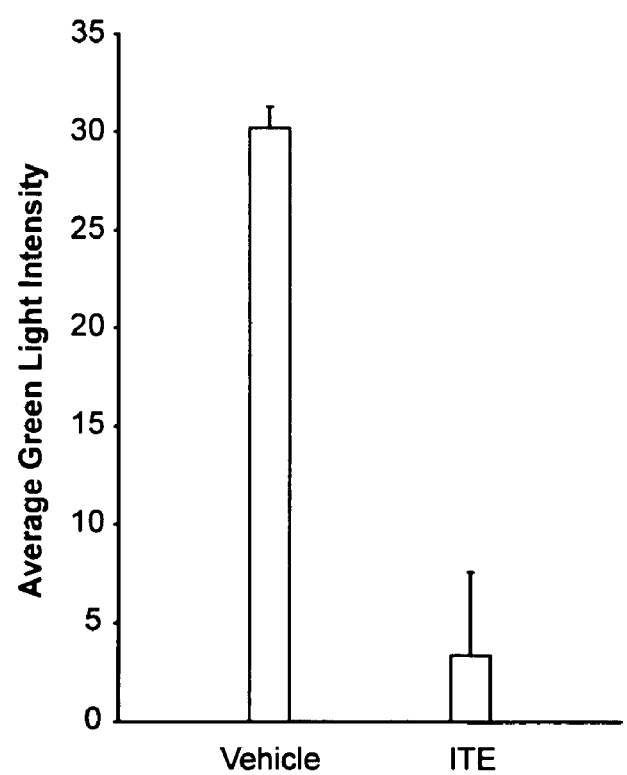
FIG. 1B shows a quantification of newly formed blood vessels in the vehicle-treated mice and the ITE-treated mice.

Results of the In Vivo Angiogenesis Inhibition Assay: Under the stimulation of bFGF, numerous neovessels grew toward the stimulant in sponges for mice injected with 20 µl of the vehicle (DMSO:propylene glycol, 1:1, v/v) each time (FIG. 1A1 to 1A3) while the growth is considerably inhibited for mice injected with 20 µl of ITE in the vehicle at a concentration of 10 µg/µl (FIG. 1A4 to 1A6). Quantification of the data presented in FIG. 1B confirms the results of visual impression.

The effective dose of about 10 mg/kg of body weight is in accord with our unpublished in vivo observations on induction of mRNA transcription of CYP1A1, an extensively characterized AhR target gene, suggesting the specificity of ITE action in angiogenesis inhibition.

Figure 2A:
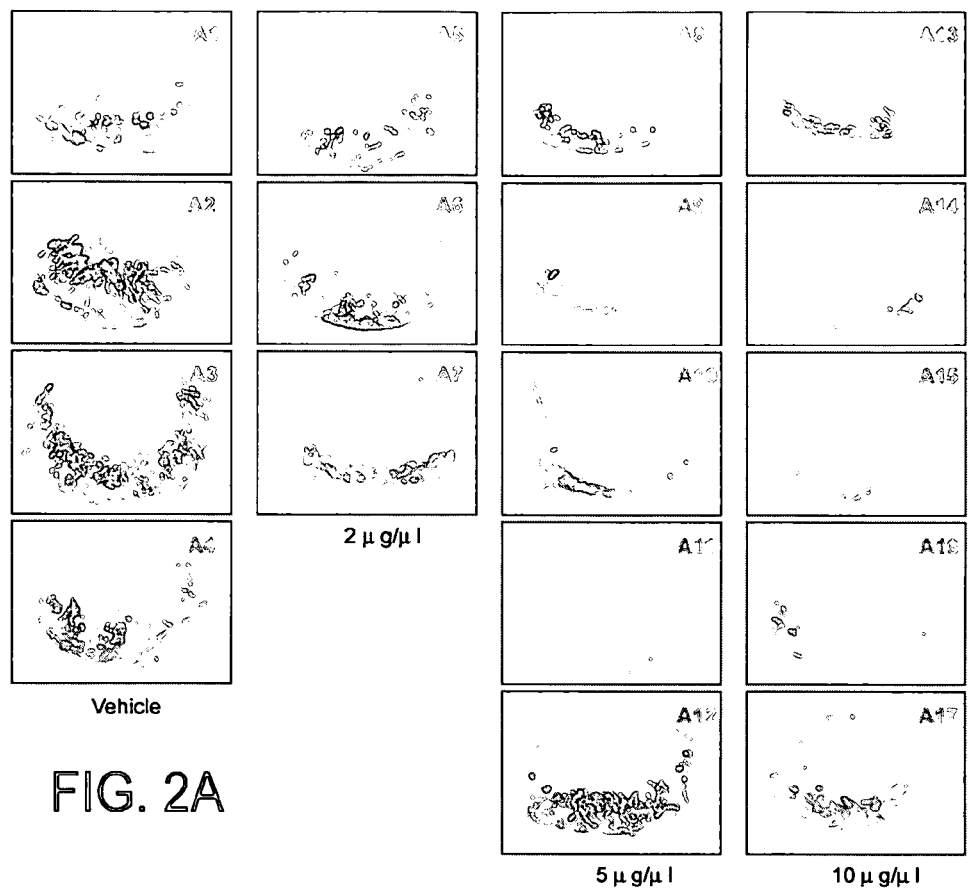
Figure 2B:
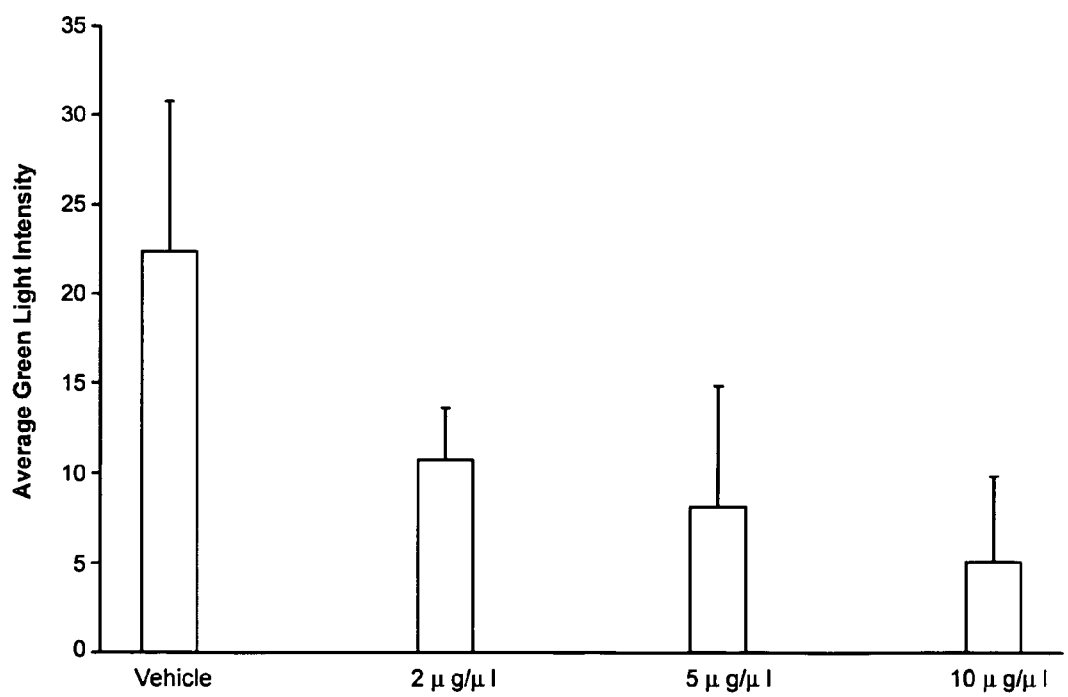
FIG. 2B shows a quantification of newly formed blood vessels in the vehicle-treated mice and the ITE-treated mice.

In another independent experiment, ITE (10 µg/µl) inhibited angiogenesis (FIG. 2A13 to FIG. 2A17) compared to vehicle-treated mice (FIG. 2A1 to FIG. 2A4). The ability of ITE to inhibit angiogenesis was also present at a concentration of 5 µg/µl (FIG. 2A8 to FIG. 2A12) and at a concentration 2 µg/µl (FIG. 2A5 to FIG. 2A7). FIG. 2B represents the quantified data from that experiment.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set for by the appended claims.

REFERENCES

Alexander, D. L., Ganem, L. G., Femandez-Salguero, P., Gonzalez, F., and Jefcoate, C. R. 1998. Aryl-hydrocarbon receptor is an inhibitory regulator of lipid synthesis and of commitment to adipogenesis. J. Cell Sci. 111(Part 22): 3311-3322.

Bello, S. M., W. Heideman, and R. E. Peterson. 2004. 2,3,7,8-tetrachlorodibenzo-p-dioxin inhibits regression of the common cardinal vein in developing zebrafish. Toxicol. Sci. 78(2):258-266.

Benedict, J. C., Lin, T. M., Loeffler, I. K., Peterson, R. E., and Flaws, J. A. 2000. Physiological role of the aryl hydrocarbon receptor in mouse ovary development. Toxicol. Sci. 56(2):382-388.

Boehm, T., Folkman, J., Browder, T., and O'Reilly M. S. 1997. Antiangiogenic therapy of experimental cancer does not induce acquired drug resistance. Nature. 390(6658): 404-407.

Bracken, C. P., Whitelaw, M. L., and Peet, D. J. 2003. The hypoxia-inducible factors: key transcriptional regulators of hypoxic responses. Cell. Mol. Life Sci. 60:1376-1393.

Bradshaw, T. D. Trapani, D. A. and Westwell, A. D. 2002. The aryl hydrocarbon receptor in anticancer drug discovery: friends or foe? Curr. Pharm. Design. 8:2475-2490.

Bryant, P. L., Clark, G. C., Probst, M. R., and Abbott, B. D. 1997. Effects of TCDD on Ah receptor, ARNT, EGF, and TGF-alpha expression in embryonic mouse urinary tract. Teratology. 55(5):326-337.

Burbach K. M., Poland A., and Bradfield C. A. 1992. Cloning of the Ah-receptor cDNA reveals a distinctive ligand-activated transcription factor. Proc. Natl. Acad. Sci. USA 89(17):8185-8189.

Caldwell, R. B., Bartoli, M., Behzadian, M. A., El-Remessy, A. E., Al-Shabrawey, M., Platt, D. H., and Caldwell, R. W. 2003. Vascular endothelial growth factor and diabetic retinopathy: pathophysiological mechanisms and treatment perspectives. Diab./Metab. Res. Rev. 19(6):442-455.

Carlson, D. B. and Perdew, G. H. 2002. A dynamic role for the Ah receptor in cell signaling? Insights from a diverse group of Ah receptor interacting proteins. J. Biochem. Mol. Toxicol. 16(6):317-325.

Carmeliet, P. 2004. Manipulating angiogenesis in medicine. J. Inter. Med. 255:538-561.

Chan, W. K., Yao, G., Gu, Y. Z., and Bradfield, C. A. 1999. Cross-talk between the aryl hydrocarbon receptor and hypoxia inducible factor signaling pathways. Demonstration of competition and compensation. J. Biol. Chem. 274: 12115-12123.

Choi, E. J., Toscano, D. G., Ryan, J. A., Riedel, N., and Toscano, W. A. Jr. 1991. Dioxin induces transforming growth factor-alpha in human keratinocytes. J. Biol. Chem. 266(15):9591-9597.

Davis, J. W. Jr., Burdick, A. D., Lauer, F. T., and Burchiel, S. W. 2003. The aryl hydrocarbon receptor antagonist, 3' methoxy-4' nitroflavone, attenuates 2,3,7,8-tetrachlorodibenzo-p-dioxin-dependant regulation of growth factor signaling and apoptosis in the MCF-10A cell line. Toxicol. Appl. Pharmacol. 188(1):42-49.

Distler, J. H. W., Hirth, A., Kurowska-Stolarska, M., Gay, R. E., Gay, S., and Distler, O. 2003. Angiogenic and angiostatic factors in the molecular control of angiogenesis. Quart. J. Nuc. Med. 47(3):149-161.

Dredge, K., Dalgleish, A. G., and Marriott, J. B. 2003. Angiogenesis inhibitors in cancer therapy. Curr. Opin. Inves. Drugs. 4(6):667-674.

Elder, J. T., Nair, R. P., Henseler, T., Jenisch, S., Stuart, P., Chia, N., Christophers, E., and Voorhees, J. J. 2001. The genetics of psoriasis 2001: the odyssey continues. Arch. Dermatol. 137(11):1447-1454.

Elizondo, G., Fernandez-Salguero, P., Sheikh, M. S., Kim, G. Y., Fomace, A. J., Lee, K. S., and Gonzalez, F. J. 2000. Altered cell cycle control at the G(2)/M phases in aryl hydrocarbon receptor-null embryo fibroblast. Mol. Pharmacol. 57(5):1056-1063.

Enan, E., El-Sabeawy, F., Scott, M., Overstreet, J., and Lasley, B. 1998. Alterations in the growth factor signal transduction pathways and modulators of the cell cycle in endocervical cells from macaques exposed to TCDD. Toxicol. Appl. Pharmacol. 151(2):283-293.

Eskens, F. 2004. Angiogenesis inhibitors in clinical development; where are we now and where are we going? Brit. J. Cancer. 90:1-7.

Fernandez-Salguero, P., Pineau, T., Hilbert, D. M., McPhail, T., Lee, S. S., Kimura, S., Nebert, D. W., Rudickoff, S., Ward, J. M., and Gonzalez, F. J. 1995. Immune system impairment and hepatic fibrosis in mice lacking the dioxin-binding Ah receptor. Science. 268:722-726.

Folkman, J. 1971. Tumor angiogenesis: therapeutic implications. N. Engl. J. Med. 285:1182-1186.

Folkman, J. 1995. Seminars in Medicine of the Beth Israel Hospital, Boston. Clinical applications of research on angiogenesis. N. Engl. J. Med. 333(26):1757-1763.

Folkman, J. 2001. Angiogenesis-dependent diseases. Semin. Oncol. 28:536-542.

Gradin, K., McGuire, J., Wenger, R. H., Kvietikova, I., Fhitelaw, M. L., Toftgard, R., Tora, L., Gassmann, M., and Poellinger, L. 1996. Functional interference between hypoxia and dioxin signal transduction pathways: competition for recruitment of the Arnt transcription factor. Mol. Cell. Biol. 16(10):5221-5231.

Giatromanolaki, A. and A. L Harris. 2001. Tumor hypoxia, hypoxia signaling pathways and hypoxia inducible factor expression in human cancer. Anticancer Res. 21 (6B): 4317-4324.

Grzywacz, P., Sicinski, R. R., and DeLuca, H. F. 2003. A concise synthesis of an AHR endogenous ligand with the indolecarbonylthiazole skeleton. Heterocycles. 60 (5): 1219-1224.

Harada, K., Lu, S., Chisholm, D. M., Syrjanen, S., and Schor, A. M. 2000. Angiogenesis and vasodilation in skin warts. Association with HPV infection. Anticancer Res. 20:4519-4523.

Heimler, I., Rawlins, R. G., Owens, H., and Hutz, R. J. 1998. Dioxin perturbs, in a dose- and time-dependent fashion, steroid secretion, and induces apoptosis of human luteinized granulose cells. Endocrinology 139:4373-4379.

Hudson, L. G., Toscano, W. A. Jr., and Greenlee, W. F. 1986. 2,3,7,8-Tetrachlorodibenzo-p-dioxin (TCDD) modulates epidermal growth factor (EGF) binding to basal cells from a human keratinocyte cell line. Toxicol. Appl. Pharmacol. 82(3):481-492.

Ivnitski-Steele, I. D. and M. K. Walker. 2003. Vascular endothelial growth factor rescues 2,3,7,8-tetrachlorodibenzo-p-dioxin inhibition of coronary vasculogenesis. Birth Defects Res. 67(7):496-503.

Kerkvliet, N. I. 2002. Recent advances in understanding the mechanisms of TCDD immunotoxicity. Internatl. Immunopharmacol. 2(2-3):277-291.

Klein, R., Klein, B. E., Moss, S. E., Davis, M. D., and DeMets, D. L. 1984. The Wisconsin epidemiologic study of diabetic retinopathy. II. Prevalence and risk of diabetic retinopathy when age at diagnosis is less than 30 years. Arch. Ophthalmol. 102(4):520-526.

Koliopanos, A., Kleeff, J., Xiao, Y., Safe, S., Zimmermann, A., Buchler, M. W., and Friess, H. 2002. Increased aryl hydrocarbon receptor expression offers a potential therapeutic target for pancreatic cancer. Oncogene. 21:6059-6070.

Lahvis, G. P., S. L. Lindell, R. S. Thomas, R. S. McCuskey, C. Murphy, E. Glover, M. Bentz, J. Southard, and C. A. Bradfield. 2000. Portosystemic shunting and persistent fetal vascular structures in aryl hydrocarbon receptor-deficient mice. Proc. Natl. Acad. Sci. USA. 97(19):10442-10447.

Lebwohl, M., Ellis, C., Gottlieb, A., Koo, J., Krueger, G., Linden, K., Shupack, J., and Weinstein, G. 1998. Cyclosporine consensus conference: with emphasis on the treatment of psoriasis. J. Am. Acad. Dermatol. 39(3):464-475.

Li, J., Yu, X., Pan, W. and Unger, R. H. 2002. Gene expression profile of rat adipose tissue at the onset of high-fat-diet obesity. Am. J. Physiol. Endocrinol. Metab. 282:E1334-E1341.

Lin, F. H., Clark, G., Birnbaum, L. S., Lucier, G. W., and Goldstein, J. A. 1991. Influence of the Ah locus on the effects of 2,3,7,8-tetrachlorodibenzo-p-dioxin on the hepatic epidermal growth factor receptor. Mol. Pharmacol. 39(3):307-313.

Louie, S. G., Park, B., and Yoon, H. 2003. Biological response modifiers in the management of rheumatoid arthritis.[erratum appears in Am J Health Syst Pharm.2003 Jun 1;60(11): 1095]. Am. J. Health-System Pharm. 60(4):346-355.

McDougal, A., Wormke, M., Calvin, J., and Safe, S. 2001. Tamoxifen-induced antitumorigenic/antiestrogenic action synergized by a selective aryl hydrocarbon receptor modulator. Cancer Res. 61(10):3902-3907.

Meyer, M., Meyer, M., Clauss, M., Lepple-Wienhues, A., Waltenberger, J., Augustin, H. G. Ziche, M., Lanz, C., Buttner, M., Rziha, H. J., and Dehio, C. 1999. A novel vascular endothelial growth factor encoded by Orf virus, VEGF-E, mediates angiogenesis via signaling through VEGFR-2 (KDR) but not VEGFR-1 (Flt-1) receptor tyrosine kinases. EMBO J. 18(2):363-374.

Mimura, J., Yamashita, K., Nakamura, K., Morita, M., Takagi, T. N., Nakao, K., Ema, M., Sogawa, K., Yasuda, M., Katsuki, M., and Fujii-Kuriyama, Y. 1997. Loss of teratogenic response to 2,3,7,8-tetrachlorodibenzo-p-dioxin (TCDD) in mice lacking the Ah (dioxin) receptor. Gene. Cell. 2:645-654.

Nilsson, C. B. and Hakansson, H. 2002. The retinoid signaling system—A target in dioxin toxicity. Crit. Rev. Toxicol. 32(3):211-232.

Nukaya, M., Takahashi, Y., Gonzalez, F. J., and Kamataki, T. 2004. Aryl hydrocarbon receptor-mediated suppression of GH receptor and Janus kinase 2 expression in mice. FEBS Let. 558(1-3):96-100.

Oliver, S. J., Cheng, T. P., Banquerigo, M. L., and Brahn, E. 1995. Suppression of collagen-induced arthritis by an angiogenesis inhibitor, AGM-1470, in combination with cyclosporin: reduction of vascular endothelial growth factor (VEGF). Cell. Immunol. 166(2):196-206.

Perez-Atayde, A. R., Sallan, S. E., Tedrow, U., Connors, S., Allred, E., and Folkman, J. 1997. Spectrum of tumor angiogenesis in the bone marrow of children with acute lymphoblastic leukemia. Am. J. Path. 150(3):815-821.

Poellinger, L. 2000. Mechanistic aspects-the dioxin (aryl hydrocarbon) receptor. Food Add. Contam. 17(4):261-266.

Poland A., Glover E., and Kende A. S. 1976. Stereospecific, high affinity binding of 2,3,7,8-tetrachlorodibenzo-p-dioxin by hepatic cytosol. Evidence that the binding species is receptor for induction of aryl hydrocarbon hydroxylase. J. Biol. Chem. 251(16):4936-4946.

Powell, T. J., Ben-Bassat, H., Klein, B. Y., Chen, H., Shenoy, N., McCollough, J., Narog, B., Gazit, A., Harzstark, Z., Chaouat, M., Levitzki, R., Tang, C., McMahon, J., Shawver, L., and Levitzki, A. 1999. Growth inhibition of psoriatic keratinocytes by quinazoline tyrosine kinase inhibitors. Brit. J. Dermatol. 141(5):802-810.

Puga, A., Barnes, S. J., Dalton, T. P., Chang, C. Y., Knudsen, E. S., and Maier, M. A. 2000. Aromatic hydrocarbon receptor interaction with the retinoblastoma protein potentiates repression of E2F-dependent transcription and cell cycle arrest. J. Biol. Chem. 275(4):2943-2950.

Puga, A., C. R. Tomlinson, and Y. Xia. 2005. Ah receptor signals cross-talk with multiple developmental pathways. Biochem. Pharmacol. 69(2):199-207.

Quintero, M., Mackenzie, N., and Brennan, P. A. 2004. Hypoxia-inducible factor I (HIF-1) in cancer. EJSO. 30(5): 465-468.

Rupnick, M. A., Rupnick, M. A., Panigrahy, D., Zhang, C. Y., Dallabrida, S. M., Lowell, B. B., Langer, R., and Folkman, M. J. 2002. Adipose tissue mass can be regulated through the vasculature. Proc. Natl. Acad. Sci. USA. 99(16):10730-10735.

Safe, S. 2001. Molecular biology of the Ah receptor and its role in carcinogenesis. Toxicol. Let. 120:1-7.

Safe, S. and McDougal, A. 2002. Mechanism of action and development of selective aryl hydrocarbon receptor modulators for treatment of hormone-dependent cancers. International Journal of Oncology. 20:1123-1128.

Safe, S., and Wormke, M. 2003. Inhibitory aryl hydrocarbon receptor-estrogen receptor a cross-talk and mechanisms of action. Chem. Res. Toxicol. 16(7):807-816.

Schmidt, J. V., Su, G. H., Reddy, J. K., Simon, M. C., and Bradfield, C. A. 1996. Characterization of a murine Ahr null allele: involvement of the Ah receptor in hepatic growth and development. Proc. Natl. Acad. Sci. USA. 93:6731-6736.

Schmidt, J. V. and Bradfield, C. A. 1996. Ah receptor signaling pathways. Ann. Rev. Cell Dev. Biol. 12:55-89.

Shimba, S., Wada, T., and Tezuka, M. 2001. Aryl hydrocarbon receptor (AhR) is involved in negative regulation of adipose differentiation in 3T3-L1 cells: AhR inhibits adipose differentiation independently of dioxin. J. Cell Sci. 114 (15):2809-2817.

Sjolie, A. K., Stephenson, J., Aldington, S., Kohner, E., Janka, H., Stevens, L., and Fuller, J. 1997. Retinopathy and vision loss in insulin-dependent diabetes in Europe. The EURODIAB IDDM Complications Study. Ophthalmology. 104(2):252-260.

Sone, H., Kawakami, Y., Sakauchi, M., Nakamura, Y., Takahashi, A., Shimano, H., Okuda, Y., Segawa, T., Suzuki, H., and Yamada, N. 2001. Neutralization of vascular endothelial growth factor prevents collagen-induced arthritis and ameliorates established disease in mice. Biochem. Biophy. Res. Comm. 281(2):562-568.

Song, J, Clagett-Dame, M., Peterson, R. E., Hahn, M. K., Westler, W. M., Sicinski, R. R., and DeLuca, H. F. 2002. A ligand for the aryl hydrocarbon receptor isolated from lung. Proc. Natl. Acad. Sci. USA. 99(23):14694-14699.

Stout, A. U. and Stout, J. T. 2003. Retinopathy of prematurity. Pediat. Clin. N. Am. 50(1):77-87.

Tian, H., S. L. McKnight, and D. W. Russell. 1997. Endothelial PAS domain protein 1 (EPAS1), a transcription factor selectively expressed in endothelial cells. Genes Develop. 11(1):72-82.

Vorderstrasse, B. A., Steppan, L. B., Silverstone, A. E., and Kerkvliet, N. I. 2001. Aryl hydrocarbon receptor-deficient mice generate normal immune responses to model antigens and are resistant to TCDD-induced immune suppression. Toxicol. Appl. Pharmacol. 171(3):157-164.

Walisser, J. A., M. K. Bunger. E. Glover, C. A. Bradfield. 2004. Gestational exposure of Ahr and Arnt hypomorphs to dioxin rescues vascular development. Proc. Natl. Acad. Sci. USA. 101(47):16677-16682.

Whitlock, J. P. Jr. 1999. Induction of cytochrome P4501A1. Ann. Rev. Pharmacol. Toxicol. 39:103-125.

Yang, C., Boucher, F., Tremblay, A., and Michaud, J. L. 2004. Regulatory interaction between aryl hydrocarbon receptor and SIMI, two basic Helix-Loop-Helix PAS proteins involved in the control of food intake. J. Biol. Chem. 279 (10):9306-9312.

Zaher, H., Fernandez-Salguero, P. M., Letterio, J., Sheikh, M. S., Fornace, A. J. Jr., Roberts, A. B., and Gonzalez, F. J. 1998. The involvement of aryl hydrocarbon receptor in the activation of transforming growth factor-beta and apoptosis. Mol. Pharmacol. 54(2):313-321.

Zhang, H. and Bicknell, R. 2001. Therapeutic inhibition of angiogenesis. In Methods in Molecular Medicine. Vol. 46: Angiogenesis Protocols. Murray, J. C. (ed.). Humana Press Inc., Totawa, N.J.

The invention claimed is:

1. A method for treating an angiogenesis-implicated disorder, wherein the disorder is selected from the group consisting of retinopathies, psoriasis, rheumatoid arthritis, and obesity comprising the steps of:
    selecting a subject predisposed to the angiogenesis-implicated disorder; and
    administering an amount of an aryl hydrocarbon receptor ligand effective to inhibit angiogenesis, the ligand having a formula of:

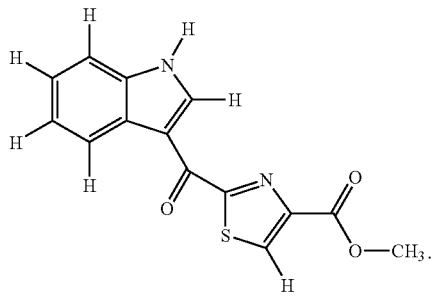

2. The method of claim 1, wherein the step of administering the aryl hydrocarbon receptor ligand is selected from the group consisting of capsules, creams, lozenges, tablets and injection.

3. The method of claim 1, wherein the ligand is combined with a pharmaceutically acceptable carrier.

4. The method of claim 1, wherein the patient is dosed twice a day.

5. The method of claim 1, additionally comprising the step of supplying a maintenance dose of the ligand.

6. The method of claim 1, wherein the concentration of the ligand within the patient's blood is determined after administration.

7. A method for treating an angiogenesis-implicated disorder, wherein the disorder is selected from the group consisting of retinopathies, psoriasis, rheumatoid arthritis, and obesity, comprising the steps of:
    selecting a subject predisposed to the angiogenesis-implicated disorder; and
    administering an amount of an aryl hydrocarbon receptor ligand effective to inhibit angiogenesis, the ligand having a formula of:

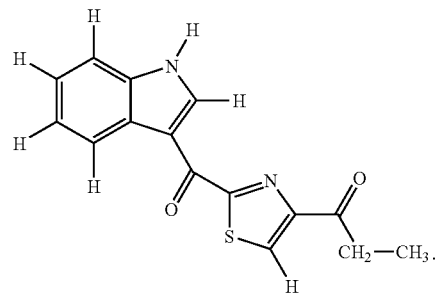

8. The method of claim 7, wherein the step of administering the aryl hydrocarbon receptor ligand is selected from the group consisting of capsules, creams, lozenges, tablets and injection.

9. The method of claim 7, wherein the ligand is combined with a pharmaceutically acceptable carrier.

10. The method of claim 7, wherein the patient is dosed twice a day.

11. The method of claim 7, additionally comprising the step of supplying a maintenance dose of the ligand.

12. The method of claim 7, wherein the concentration of the ligand within the patient's blood is determined after administration.

* * * * *

UNITED STATES PATENT AND TRADEMARK OFFICE
CERTIFICATE OF CORRECTION

PATENT NO.       : 7,419,992 B2
APPLICATION NO.  : 11/402581
DATED            : September 2, 2008
INVENTOR(S)      : Hector F. DeLuca et al.

It is certified that error appears in the above-identified patent and that said Letters Patent is hereby corrected as shown below:

In the Specification

| | | | | |
|---|---|---|---|---|
| Column 1,  | line 56 | "Femandez" | should be | --Fernandez-- |
| Column 2,  | line 45 | "Amt"      | should be | --Arnt--      |
| Column 2,  | line 63 | "(Ld.)"    | should be | --Id.--       |
| Column 13, | line 7  | "Femandez" | should be | --Fernandez-- |
| Column 14, | line 9  | "Fomace"   | should be | --Fornace--   |

Signed and Sealed this
Thirteenth Day of May, 2014

Michelle K. Lee
*Deputy Director of the United States Patent and Trademark Office*